United States Patent
Garcia Gros et al.

(10) Patent No.: US 8,795,609 B2
(45) Date of Patent: Aug. 5, 2014

(54) MAGNETIC PARTICLE WASHING STATION

(75) Inventors: Luis Miguel Garcia Gros, Barcelona (ES); Mark Talmer, Pepperell, MA (US); Gerhardt P. Schroeder, Londonderry, NH (US); Paul C. Dahlstrom, Hollis, NH (US); Jose Serra Domènech, Barcelona (ES)

(73) Assignee: Biokit, S.A., Barcelona (ES)

( * ) Notice: Subject to any disclaimer, the term of this patent is extended or adjusted under 35 U.S.C. 154(b) by 1207 days.

(21) Appl. No.: 11/704,138

(22) Filed: Feb. 8, 2007

(65) Prior Publication Data

US 2008/0190458 A1    Aug. 14, 2008

(51) Int. Cl.
*B01L 9/06* (2006.01)

(52) U.S. Cl.
USPC .................. 422/562; 422/561; 422/566

(58) Field of Classification Search
CPC .......................................... B03C 1/14
USPC .................. 422/562, 561, 560, 566
See application file for complete search history.

(56) References Cited

U.S. PATENT DOCUMENTS

| | | |
|---|---|---|
| 5,147,529 A | 9/1992 | Lee et al. |
| 5,238,558 A | 8/1993 | Curtis |
| 5,512,332 A | 4/1996 | Liberti et al. |
| 5,540,890 A | 7/1996 | Clark et al. |
| 5,599,501 A | 2/1997 | Carey et al. |
| 5,827,478 A | 10/1998 | Carey |
| 5,888,835 A | 3/1999 | Bushnell et al. |
| 5,932,108 A | 8/1999 | Brunsting |
| 5,985,671 A | 11/1999 | Leistner et al. |
| 6,016,712 A | 1/2000 | Warden et al. |
| 6,149,872 A | 11/2000 | Mack et al. |
| 6,292,680 B1 | 9/2001 | Somogyi et al. |
| 6,413,420 B1 | 7/2002 | Foy et al. |
| 6,562,239 B2 | 5/2003 | Foy et al. |
| 6,623,983 B1* | 9/2003 | Terstappen et al. ........... 436/526 |
| 6,755,161 B2 | 6/2004 | Grundl et al. |
| 6,808,873 B2 | 10/2004 | Murphy et al. |
| 2003/0044323 A1 | 3/2003 | Diamond et al. |
| 2003/0127396 A1* | 7/2003 | Siddiqi ........................ 210/695 |

(Continued)

FOREIGN PATENT DOCUMENTS

| | | |
|---|---|---|
| EP | 0712000 | 9/1995 |
| EP | 0806665 | 5/1997 |

(Continued)

OTHER PUBLICATIONS

Siemens Global website @ http://diagnostics.siemens.com/webapp/wcs/stores/servlet/Product, for ACS:180® SE Automated Chemiluminescence System accessed Jun. 13, 2007, © Siemens AG, 2007.

(Continued)

*Primary Examiner* — Natalia Levkovich
(74) *Attorney, Agent, or Firm* — Burns & Levinson LLP (57) ABSTRACT

Embodiments of the invention relate to a clinical instrument analyzer system for the automatic analysis of patient samples. In one embodiment, the analyzer may be used to analyze bodily fluid samples, such as blood, plasma, serum, urine or cerebrospinal fluid, for example. Embodiments of the invention relate to an apparatus and method, for example, an immunoassay method, for separating out target molecules in a magnetic field and then analyzing those target molecules with a luminometer.

13 Claims, 8 Drawing Sheets

(56) References Cited

U.S. PATENT DOCUMENTS

| | | |
|---|---|---|
| 2004/0142384 A1 | 7/2004 | Cohen et al. |
| 2004/0265903 A1* | 12/2004 | Mueller et al. ............ 435/7.1 |
| 2005/0202573 A1 | 9/2005 | Atsushi et al. |
| 2005/0271550 A1 | 12/2005 | Talmer et al. |
| 2006/0081539 A1 | 4/2006 | Safar |
| 2006/0127942 A1 | 6/2006 | Straume et al. |

FOREIGN PATENT DOCUMENTS

| | | |
|---|---|---|
| EP | 0889328 | 10/1997 |
| JP | 1028561 | 1/1989 |
| JP | 07-181188 | 7/1995 |
| JP | 8146001 | 6/1996 |
| JP | 10123136 | 5/1998 |
| JP | 2000111557 | 4/2000 |
| JP | 2001-091521 | 4/2001 |
| JP | 2001116752 | 4/2001 |
| JP | 2005-028201 | 2/2005 |
| WO | WO98/18008 | 4/1998 |
| WO | 03/020427 | 3/2003 |

OTHER PUBLICATIONS

International Search Report for International Application No. PCT/US2008/52903, dated Jun. 27, 2008 (2 pages).

International Preliminary Report on Patentability dated Aug. 11, 2009, received in PCT/US2008/052903.

Office action in the counter part Canadian patent application No. 2,676,042 on Jan. 16, 2014 (2 pages).

* cited by examiner

MAGNETIC PARTICLE WASHING STATION

FIELD OF THE INVENTION

The present invention relates to a clinical instrument analyzer system and specifically to a magnetic particle washing station.

BACKGROUND OF THE INVENTION

Separation, isolation, and concentration are process steps common to a chemical analysis. Often, these steps are taken to remove interfering substances so that a subsequent chemical analysis can be performed. This separation stage can be performed in several ways including solvent extraction, solvent evaporation, and resin exchange. Magnetic separation, another technique for removing interfering substances, is a process of separation, isolation, and concentration where the sought-for substance is attached or bound to magnetic particles. The magnetic particles offer advantages of handling including speed, convenience, and low energy input. The use of magnetic particles is particularly suited to handling samples of small volume.

Previous magnetic separation techniques have involved the movement of a sample substance through a series of magnets. This technique, although effective, is cumbersome and is subject to mechanical failures. Additionally, since during the separation process the samples are moving through a series of magnets, it is difficult to control the environment surrounding the samples, as the samples cannot be completely enclosed. Therefore, it would be desirable to eliminate the series of magnets and provide a magnetic separation technique where samples do not have to be passed through several magnets to complete the separation process.

SUMMARY OF THE INVENTION

In satisfaction of the above-mentioned needs and others, the present teachings relate to an apparatus for manipulating magnetic particles in a vial comprising one or more pipettes, a receiving member for holding the vial containing magnetic particles, and a magnet array for isolating the magnetic particles in the vial. In some embodiments, the magnet array comprises a first magnet having an upper horizontal surface, wherein a north pole of the first magnet is positioned to face the vial positioned in the receiving member, a spacer having an upper horizontal surface, wherein the spacer is positioned on the upper horizontal surface of the first magnet, a second magnet having an upper horizontal surface, wherein the second magnet is positioned on the upper horizontal surface of the spacer, wherein a north pole of the second magnet is positioned to face the vial, a third magnet positioned on the upper horizontal surface of the second magnet, wherein a south pole of the third magnet is positioned to face the vial, wherein, said magnet array generates a magnetic field for manipulating the magnetic particles in the vial.

In one embodiment the spacer is manufactured from any of the following materials: aluminum, carbon fiber, polymers, other non-magnetic materials, and combinations thereof. In one embodiment, the magnet array is in a fixed position. In another embodiment, the magnet array is moveable. In some embodiments, the magnet array comprises a material including neodymium-iron-boron (Nd—Fe—B), typically known as neodymium, samarium-cobalt (Sm—Co), alnico, or hard ferrite (ceramic). In one embodiment, the system further comprises any one of the following: a humidity detector, a humidity regulator, a spring finger, a humidity regulated vial chamber, a temperature regulator, an aspirator pipette, or an injector pipette. In some embodiments, the humidity and/or temperature are regulated. In some embodiments, the ratio of the magnet arrays to vial receiving members is 1:1. In certain embodiments, the horizontal surface of the first and second magnets is greater than the vertical surface of those magnets. In some embodiments, the south pole of the first and second magnets face the vial and the north pole of the third magnet faces the vial.

Another embodiment of the present teachings relates to a magnetic washing module for washing magnetic particles in a vial, comprising one or more pipettes, one or more magnets, a receiving member, and a humidity detector for determining the humidity in the magnetic washing module.

Another aspect of the present teachings relates to a method for moderating magnetic particle aggregation in a diagnostic assay comprising providing a magnetic washing module comprising one or more pipettes, one or more magnets, and a vial chamber; introducing a vial containing magnetic particles into the vial chamber of the magnetic washing module; and moderating the humidity in the vial chamber to provide a predetermined relative humidity. In one embodiment, the humidity is regulated by controlling the rate of fluid injection into the vial. In another embodiment, the humidity is regulated by controlling the rate of aspiration. In another embodiment, the magnetic washing module further comprises a humidity detector.

Another embodiment relates to a magnetic washing module for washing magnetic particles in a vial comprising one or more pipettes, one or more magnets, and a humidity detector.

Another embodiment relates to a method for luminometric analysis, in which a sample vial contains a patient's sample and magnetic particles which bind the target molecules in the sample, comprising transporting the sample vial to a magnetic washing module, applying a magnetic field to the sample vial containing the target components and magnetic particles through one wall of the sample vial by a magnetic array, injecting and aspirating a wash fluid in the sample vial to wash the magnetic particles, and transporting the sample vial from the magnetic washing module to a luminometer.

BRIEF DESCRIPTION OF THE DRAWINGS

These embodiments and other aspects of this invention will be readily apparent from the detailed description below and the appended drawings, which are meant to illustrate and not to limit the invention, and in which.

DESCRIPTION

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

Embodiments of the invention relate to a clinical instrument analyzer system for the automated analysis of patient samples. In one embodiment, the analyzer may be used to analyze bodily fluid samples, such as blood, plasma, serum, urine or cerebrospinal fluid, for example. Embodiments of the invention relate to an apparatus and method, for example, an immunoassay method, for separating out target molecules in a magnetic field and then analyzing those target molecules with a luminometer.

Figure 1:
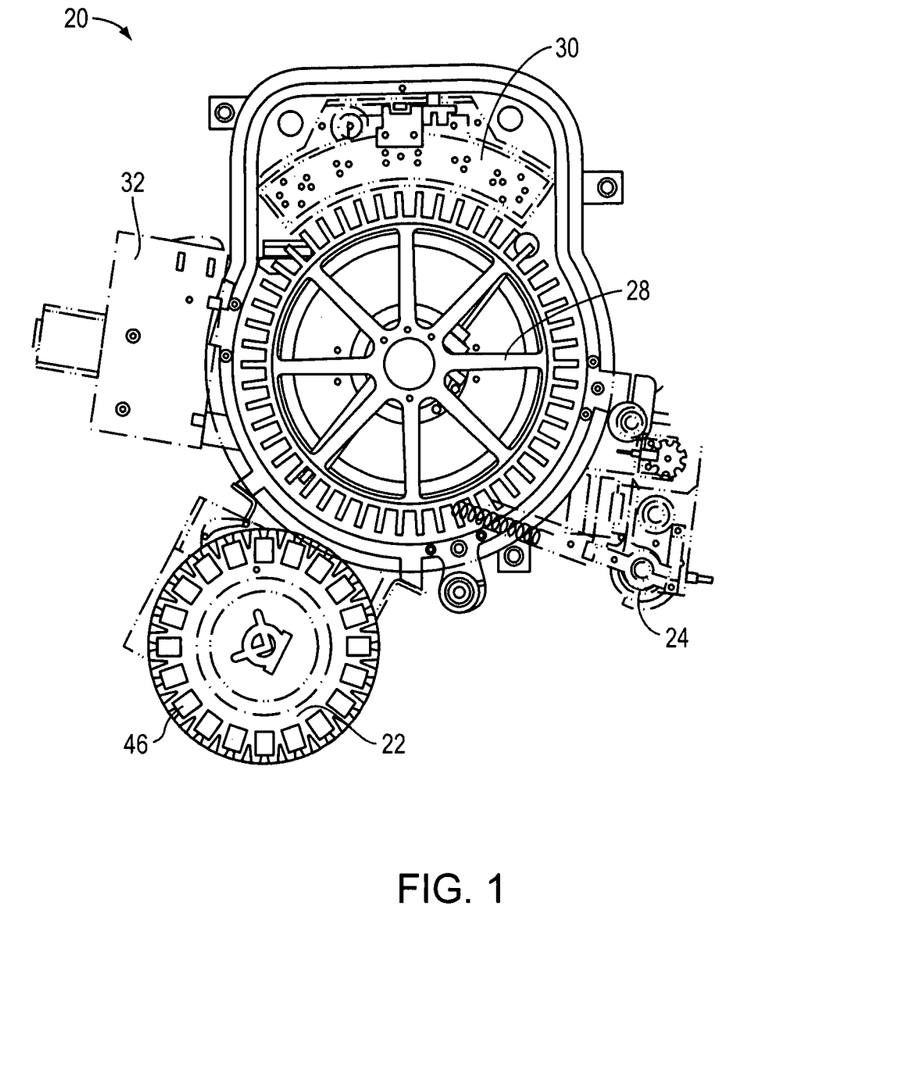
FIG. 1 is a top view of the clinical instrument analyzer system according to an exemplary embodiment of the present invention.

FIG. 1 is a top view of the clinical instrument analyzer system according to an embodiment of the present invention. The illustrated clinical instrument analyzer system 20 contains one or more stations or modules for treatment and analysis of patient samples contained in a vial 46. The vial 46 may be a cuvette, test tube, or any other receptacle for holding a sample. In one embodiment, the clinical instrument analyzer system 20 includes at least the following: a vial loader 22, a sample station (not shown), a reagent station (not shown), a carousel 28, a magnetic washing module 30, a plurality of pipettes 24, a luminometer 32, a humidity regulator 76 (see FIG. 2), and a heater or temperature regulator 77 (see FIG. 2) to incubate the sample vial 46.

In one embodiment, the vial loader 22 holds a plurality of vials 46. The vial loader 22 may, for example, load vials 46 onto the carousel 28 as described in the concurrently filed U.S. patent application entitled "Apparatus and Methods for Dispensing Sample Holders". In some embodiments, the vial loader 22 comprises a rotatable vial loader carousel with vertical slots to hold stacks of vials 46. The vials 46 are stacked in a sleeve and the sleeve may be inserted into the vial loader 22. The vial loader 22 expels vials 46 from the sleeve and loads them on to the carousel 28.

With continued reference to FIG. 1, the carousel 28, in one embodiment, holds, and distributes a plurality of vials 46 to various stations or modules in the clinical instrument analyzer system 20. The exemplary carousel 28 rotates via an attached motor and may address any one of a plurality of analyzing stations proximate to the carousel 28. In one embodiment, a transfer arm (not shown) moves vials 46 from the carousel 28 to the various analyzing stations of the clinical instrument analyzer system 20.

The plurality of analyzing stations include, for example, a reagent station (not shown), a magnetic washing module 30, a sample adding station (not shown) and an incubation station (not shown). Other stations for processing the sample may also be available and the invention is not limited to these stations.

A sample is introduced into the vial 46 at the sample adding station. Then, the reagent station (not shown), in one embodiment, deposits the required reagents into the vial 46 on which a desired analysis will be performed.

In one embodiment, the reagent station includes a plurality of reagent containers. The reagent containers may contain one or more reagents which may be injected from the reagent container into a vial 46. Depending on the analysis to be conducted on the sample and which target molecule is to be analyzed, the reagent station may provide one or more of rinse fluids, antibodies against the sample substance, a marker substance containing luminogens, and/or carrier particles that are magnetizable. In one embodiment, the marker substance attaches to specific antibodies directed to the target molecule in the sample. In some embodiments, the magnetizable carrier particles (magnetic particles) are made of iron or any other magnetic or magnetizable material. In certain embodiments, the magnetizable particles are paramagnetic. The magnetizable particles may have a grain size, for example, in the range of about 0.5-6.0 µm, for example, 0.9-1.3 µm, 2.6-3.0 µm or 4.5-5.0 µm, preferably. In yet another embodiment, the exterior of the magnetizable particles are coated with a latex layer that contains specific antibodies against the target molecule. The antibodies attached to the magnetic particles and the antibodies attached to the marker substance recognize the target molecules and bind to them in an immunochemical reaction. As a result, specific complexes of magnetic particles, markers, and target molecules are formed. These specific complexes then may be examined in the luminometer.

The clinical instrument analyzer system 20 according to one embodiment of the invention includes a plurality of pipettes 24 as shown in FIG. 1. In one embodiment, one or more pipettes 24 transfer fluids, including e.g., sample fluid, reagents, water, or a wash fluid between, for example, the reagent containers and the vials 46, sample containers and the vials 46, a wash fluid container and the vials 46, or vials 46 to a wash fluid receptacle for used wash fluid.

With continued reference to FIG. 1, the luminometer 32 may be any device that measures luminescence, such as the luminescence of the luminescent marker in the specific complexes. The intensity of the luminescence serves as an indication of the presence or absence of the target molecule in the fluid sample. The luminescence radiation passes through the vial 46 and can be detected by, for example, a photodetector in the luminometer 32. In order not to distort the measurement results, the free luminogens that are not bonded to the sample molecules are removed prior to the luminescence measurement. In one embodiment, the unbonded luminogens are removed through a series of washing cycles in the magnetic washing station as described below. Once the luminescence is measured for the sample, the intensity of the luminescence is evaluated taking into account calibration relationships and calibration measurements for the concentration of the target molecule.

Figure 2:
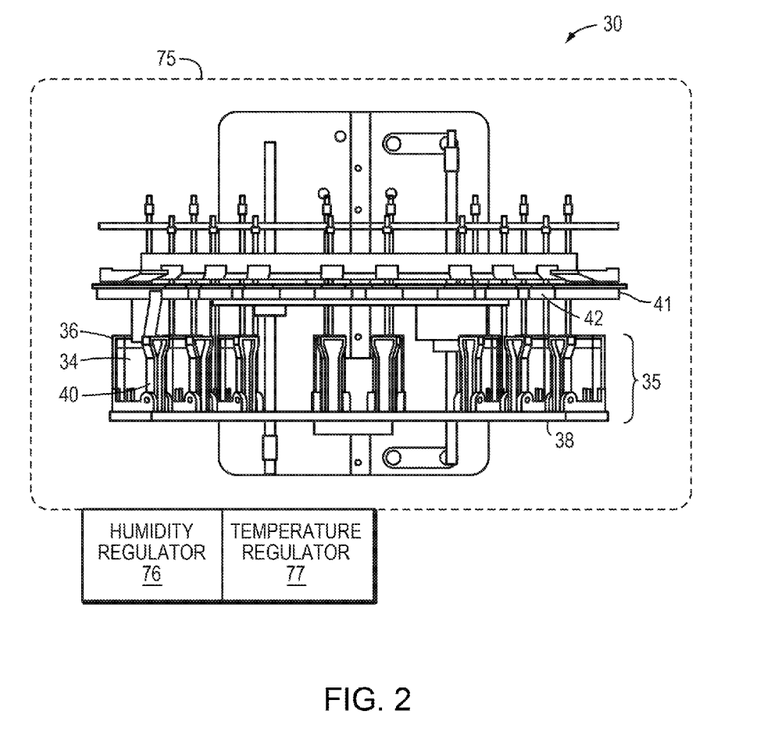
FIG. 2 is a perspective view of the magnetic washing module according to an exemplary embodiment of the present invention.

FIG. 2 is a perspective view of the magnetic washing module 30 according to an embodiment of the present invention. The exemplary magnetic washing module 30 includes the following: a base 38, one or more magnet stations 35, for example, eight magnet stations, and a vial apparatus 41, including one or more receiving members 42. According to one embodiment of the invention, each magnet station 35 comprises a magnet array 34, a magnet holder 36 and a spring finger 40. The number of stations 35 per magnetic washing module 30 is not limited to the number illustrated, but may be any number. For example, two, three, four, five, six, eight or more magnet stations 35 may be positioned in the magnetic washing module 30 (not shown).

With continued reference to FIG. 2, the exemplary magnet holder 36 holds a magnet array 34. The magnet holder 36 of the magnet station 35 may be made of, for example, stainless steel, aluminum, other metals, plastics, or ceramics. In one embodiment, the magnet holder 36 is L-shaped with the magnet array 34 affixed to interior surface of the vertical section of the L.

With continued reference to FIG. 2, the base 38 of the magnet station 35 may be made of, for example, stainless steel, aluminum, other metals, plastics, or ceramics. The magnet station 35 may be releasably attached to the base 38 or the magnetic station 35 may be fixed to the base 38.

With continued reference to FIG. 2, the spring finger 40 may be attached to the magnet holder 36 at the end of the horizontal section of the L via a spring mechanism (not shown). The spring mechanism permits the magnet holder 36 to securely hold a vial 46 against the magnet array 34. In one embodiment, the spring finger 40 is comprised of plastic, but its composition is not limited to plastic and may include any polymer, ceramic, or metal. In another embodiment, the spring finger 40 is biased towards the magnet array 34. When the vial 46 is introduced into the magnet holder 35, the spring finger 40 moves away from the magnet array 34 to accommodate the vial 46.

Figure 3:
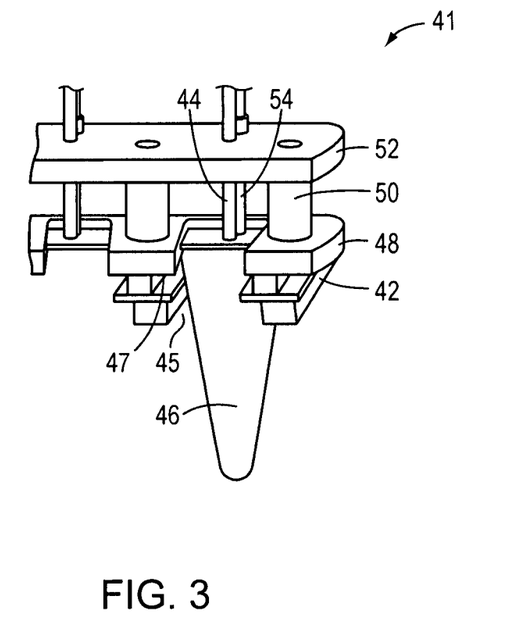
FIG. 3 is a perspective view of a vial in the vial apparatus of the magnetic washing module according to an exemplary embodiment of the present invention.

FIG. 3 is a perspective view of a vial 46 in the vial apparatus 41 of the magnetic washing module 30 according to an embodiment of the present invention. The vial apparatus 41 includes a receiving member 42 with chamfers 47, one or more aspirator pipettes 44, a vial cover 48, one or more spacers 50, an injector plate 52, and one or more injector pipettes 54. The vial apparatus 41 is positioned above the magnet stations 35. The exemplary vial apparatus 41 receives the vials 46 from the carousel 28 via a transfer arm (not shown).

With continued reference to FIG. 3, in one embodiment, the receiving member 42 holds the vials 46 in position while the vials 46 are processed in the magnetic washing station 30. The receiving member 42 is sized and shaped to fit a vial. For example, the vial receiving member 42 may be rectangular, square, circular, or semi-circular in shape with an inlet 45 to receive the vial 46 of like or similar shape. The receiving member 42 may be composed of, for example, plastic, ceramic or metal. The vial 46 may be guided into place at the receiving member 42 by, for example, chamfers 47, i.e. small grooves or channels, at the inlet 45 of the receiving member 42. A transfer arm (not shown) may use, for example, a proximity sensor to confirm that it has delivered a vial 46 to each receiving member 42 that can be used. In one embodiment, the number of receiving members 42 is such that the ratio of vials 46 in a receiving member 42 to magnet stations 35 is one to one.

With continued reference to FIG. 3, each vial 46 may be placed under an aspirator pipette 44 and an injector pipette 54. The aspirator pipette 44, for example, transfers excess or residual gas, air, and/or fluid from the vial 46. The injector pipette 54, for example, supplies liquid wash solution to the vials 46. In one embodiment, both the aspirator pipette 44 and the injector pipette 54 pass through the injector plate 52 to the vial 46. In one embodiment, the aspirator pipettes 44 and injector pipettes 54 assist to keep the magnetic particles moist during the magnetic washing process. A series of washes and aspirations, for example, deposit a thin layer of liquid on the magnetic particles protecting the magnetic particles and the specific complexes from clumping and drying together. In some embodiments, a plate spacer 50 is located between the receiving member 42 and the injector plate 52. The plate spacer 50 and the injector plate 52 may be composed of, for example, plastic, ceramic, or metal.

Referring back to FIG. 2, the vial apparatus 41 and the magnet stations 35 on the base 38 each may move relative to the other in order to engage the vial 46 in the magnet station 35. In one embodiment, the base 38, including the magnetic array 34, is fixed and the vial apparatus 41 moves, for example downwards, to the base 38. In another embodiment, the vial apparatus 41 is fixed and the base 38, including the magnetic array 34, moves, for example, upwards to the vials 46 in the vial apparatus 41. The base 38 may, for example, move between a first position and a second position, relative to the vial apparatus 41. The first position may be a position in which the magnet station 35 and the vial apparatus 41 are separated by a predetermined distance. The second position may be a position in which the magnet station 35 has moved toward the vial apparatus 41 sufficiently to permit the magnet station 35 to engage the vial 46 in the vial apparatus 41. In yet another embodiment, both the vial apparatus 41 and the base 38 move.

Figure 4:
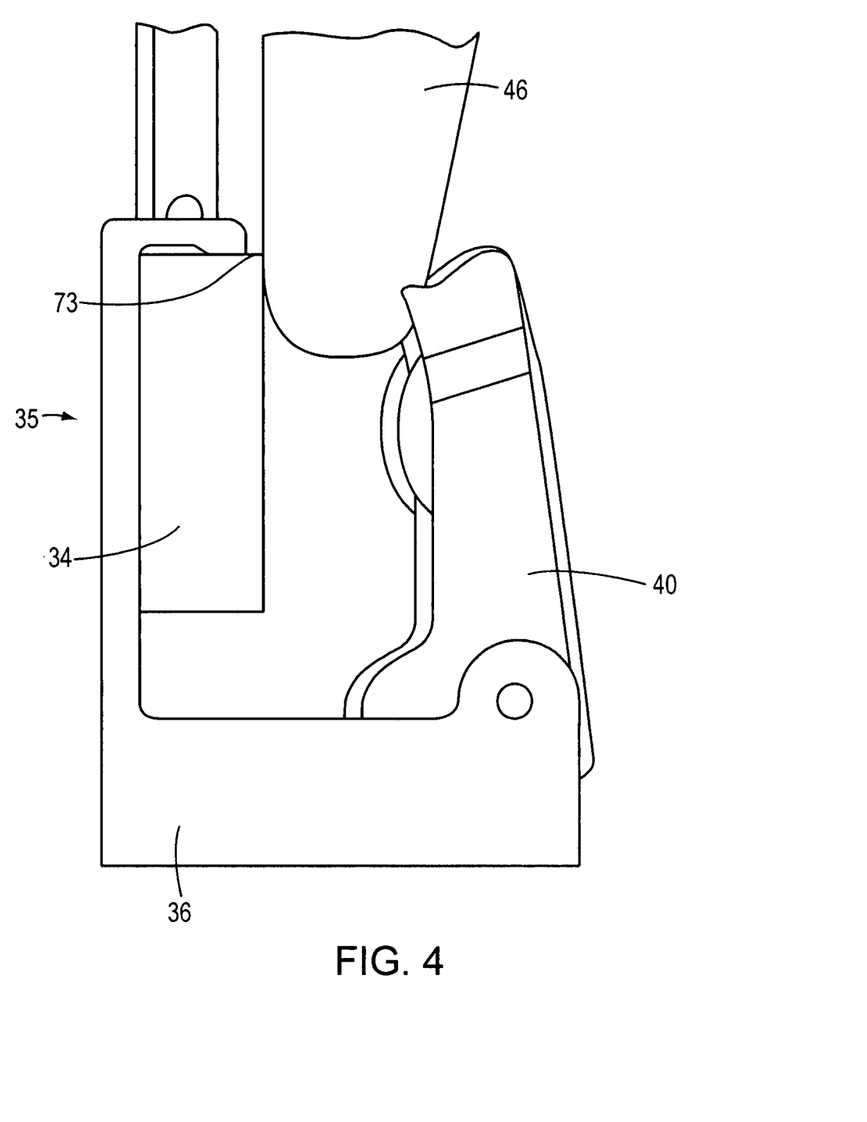
FIG. 4 is a depiction of the vial locked in the magnet washing station according to an exemplary embodiment of the present invention.

FIG. 4 depicts the vial 46 locked in the magnet station 35 according to an embodiment of the present invention. In the exemplary embodiment, when the vial 46 is locked in the magnet station 35, the wall 73 of the vial 46 proximate to the magnet array 34 is flush (i.e. in the same plane) with the magnet array 34. As the vial 46 engages the magnet station 35, the vial 46 engages and compresses a spring (not shown) contained within the spring finger 40 pushing the spring finger 40 away from the magnet array 34. The tension of the spring in the spring finger 40 holds the vial 46 in place in the magnet station 35.

Figure 5:
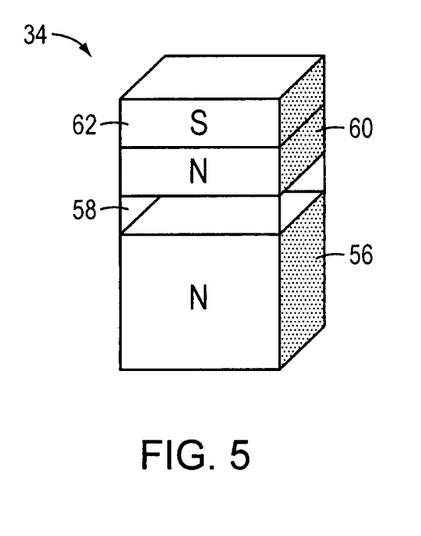
FIG. 5 is a depiction of one arrangement of the magnets according to an exemplary embodiment of the present invention.
Figure 6:
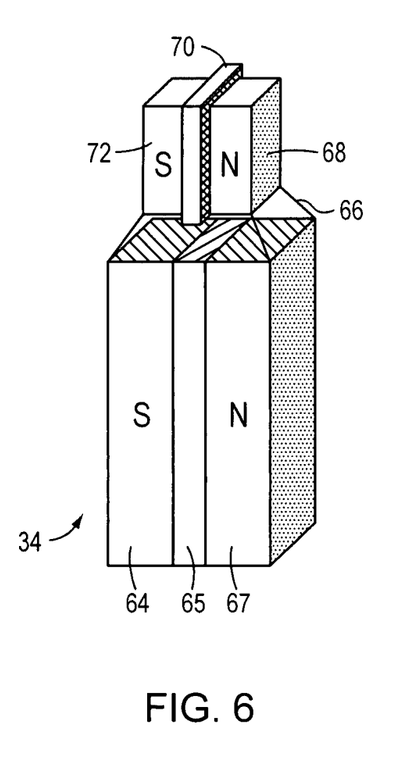
FIG. 6 is a depiction of another arrangement of the magnets according to an exemplary embodiment of the present invention.

FIGS. 5 and 6 are schematics of two embodiments of magnet array 34 configurations. The magnets may be composed of, for example, neodymium-iron-boron (Nd—Fe—B), typically known as neodymium, samarium-cobalt (Sm—Co), alnico, or hard ferrite (ceramic).

FIG. 5 depicts one embodiment of the magnet array 34 configuration including three magnets. This embodiment consists of a first magnet 56, a second magnet 60, a third magnet 62, and a spacer 58. The first magnet 56 is positioned at the bottom. The third magnet is positioned at the top, and the second magnet 60 is positioned between the first magnet 56 and the third magnet 62.

With continued reference to FIG. 5, the side of the magnet array 34 that faces the vial 46 is depicted. In one embodiment, the first magnet 56, the largest of the three magnets, has an upper horizontal surface and is positioned such that the north pole of the first magnet 56 faces the vial 46 (not shown). A spacer 58, having an upper horizontal surface, is positioned on the upper horizontal surface of the first magnet 56 between the first magnet 56 and the second magnet 60. The second magnet 60, positioned on the upper horizontal surface of the spacer 58, has an upper horizontal surface and has its north pole oriented in the same manner as the first magnet 56, i.e., facing the vial 46. The third magnet 62 is on the upper horizontal surface of the second magnet 60 and has its south pole oriented in a direction opposite to the second magnet 60 and the first magnet 56, i.e., facing the vial. In another embodiment, the magnets are arranged such that the first magnet 56 south pole and the second magnet 60 south pole face the vial 46 and the third magnet 62 north pole faces the vial 46. In other words, the orientation of the polarity of the third magnet 62 is opposite to the orientation of the polarity of the first magnet 56 and the second magnet 60.

In one embodiment, with continued reference to FIG. 5, the second magnet 60 and third magnet 62 are configured such that the horizontal axis of each magnet exceeds the vertical axis of the magnet. This orientation of the magnets produces few interactions with the magnets in the other magnet stations 35 (not shown). Thus, when arranged in the magnetic washing module 30, the magnet arrays 34 all may, for example, have the same orientation. However, the magnet arrays 34 may be arranged in varying orientations and the orientations are not limited to those illustrated.

FIG. 6 depicts another embodiment of the magnet array 34 configuration. The illustrated embodiment includes a vertical configuration of the individual magnets including a first vertical magnet 64, a second vertical magnet 65, a third vertical magnet 67, a first spacer 66, a fourth vertical magnet 68, a second spacer 70 and a fifth vertical magnet 72. In one embodiment, the first vertical magnet 64, second vertical magnet 65, the third vertical magnet 67, the fourth vertical magnet 68, and the fifth vertical magnet 72, each have a longer vertical axis than horizontal axis.

With continued reference to FIG. 6, the first vertical magnet 64, second vertical magnet 65, and third vertical magnet 67 are arranged in a Halbach array. A Halbach array is an arrangement of magnets in which the magnetic field can be augmented on one side of the array, the side facing the vial 46 (not shown), and near zero on the opposite side of the array. In one embodiment, illustrated in FIG. 6, this array may be positioned such that the first magnet 64 having its south pole facing the vial 46, a second magnet 65 adjacent the first magnet 63 with neither north nor south pole facing the vial 46, and a third magnet 67 adjacent the second magnet 65 but not the first magnet 63, having its north pole facing the vial 46. The first vertical magnet 64, second vertical magnet 65, and third vertical magnet 67 may be arranged in any other configuration that produces a magnetic field on the side of the array facing the vial 46 and a near zero magnetic field on the opposite side. Furthermore, the present teachings are not limited to three magnets on the bottom of the array. For example, four, five, six, or more could be implemented so long the magnetic field is augmented on the side facing the vial 46 and near zero on the opposite side.

Figure 7:
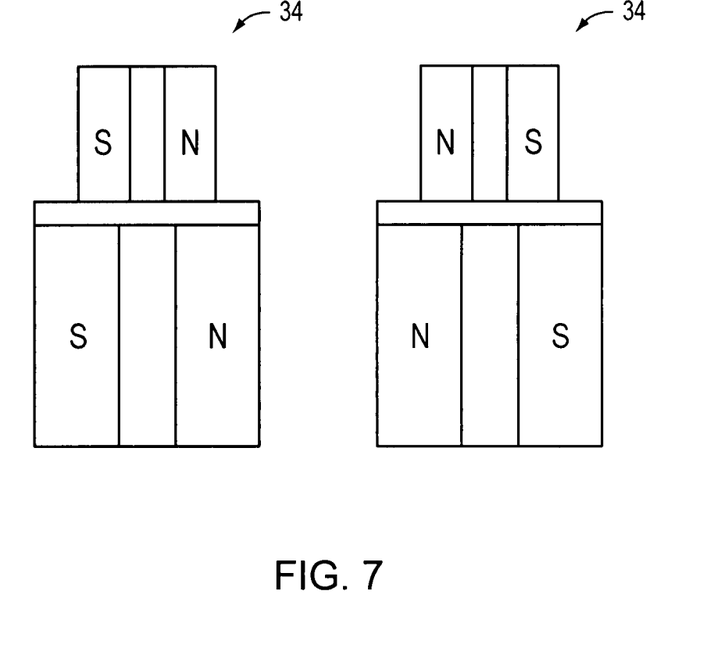
FIG. 7 is a depiction of two magnet arrangements according to an exemplary embodiment of the present invention.

With continued reference to FIG. 6, in one embodiment, the first spacer 66 is positioned on the upper horizontal surface, of the first vertical magnet 64, the second vertical magnet 65, and the third vertical magnet 67. Positioned on top of the first spacer 66 are the fourth vertical magnet 68, including a north pole facing the vial 46, a fifth vertical magnet 72, including a south pole facing the vial 46, and a second spacer 70 positioned between the fourth vertical magnet 68 and the fifth vertical magnet 72. This embodiment of the magnet array 34 configuration may cause interference effects if several magnet arrays 34 of this configuration are proximate to each other. Therefore, as shown in FIG. 7, magnet arrays 34 with this configuration should be used in mirror configurations, such that one magnet array 34 is a mirror image of an adjacent magnet array 34.

With reference to FIGS. 5 and 6, the spacers 58, 66, and 70 are sized in the range of, for example, 0.5 mm to 1.5 mm in width. The spacers 58, 66, and 70 are composed of, for example, aluminum, plastic, ceramics, carbon fiber, polymers, combinations of the foregoing, or any other non-magnetic material.

Figure 8:
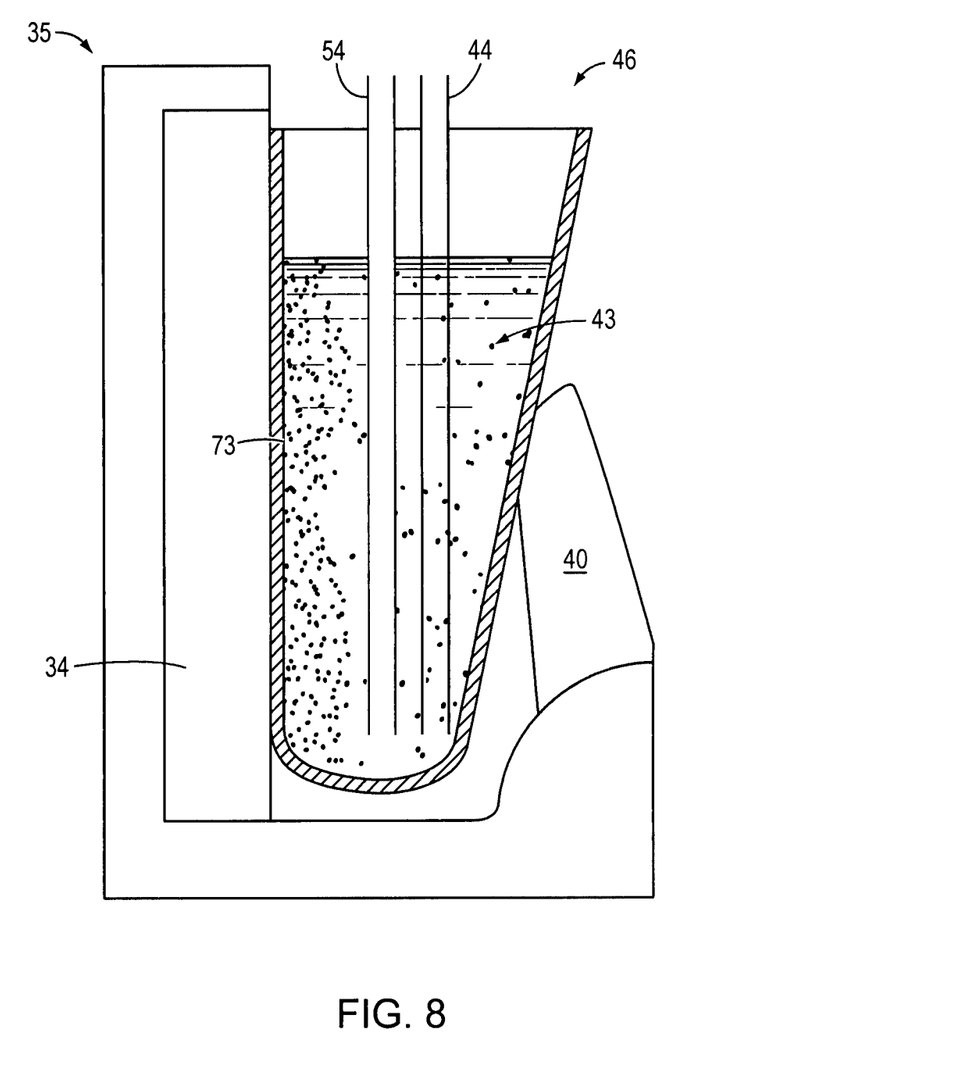
FIG. 8 is a depiction of a vial in the magnet station during a magnetic wash process according to an exemplary embodiment of the invention.

FIG. 8 depicts a vial 46 positioned in a magnet station 35 during a magnetic wash process according to one embodiment of the invention. Once the vial 46 is engaged by the magnet station 35, the magnetic field generated by the magnet array 34 attracts the specific complexes 43 of magnetic particles, markers, and target molecules. Thus, the specific complexes 43 in the vial 46 are held on the interior wall 73 of the vial 46 proximate to the magnet array 34. A series of washes and aspirations via the aspirator pipettes 44 and the injector pipette 54 coupled with the magnetic field application produces a pellet 74 of the specific complexes 43 in the vial as shown, for example, in FIGS. 9 and 10. In order to facilitate the production of the pellet 74, the magnet array 34 and the vial 46 may move relative to each other. For example, if the vial 46 is stationary, the magnet array 34 may move up and down to assist in creating the pellet 74.

Figure 9:
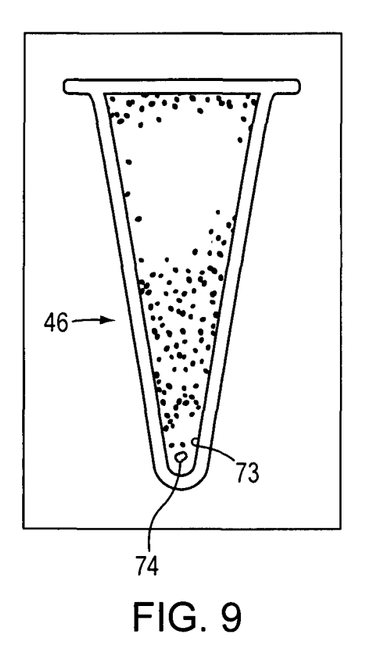
FIGS. 9 and 10 are depictions of magnetic particle pellets collected in the vial according to an exemplary embodiment of the present invention.
Figure 10:
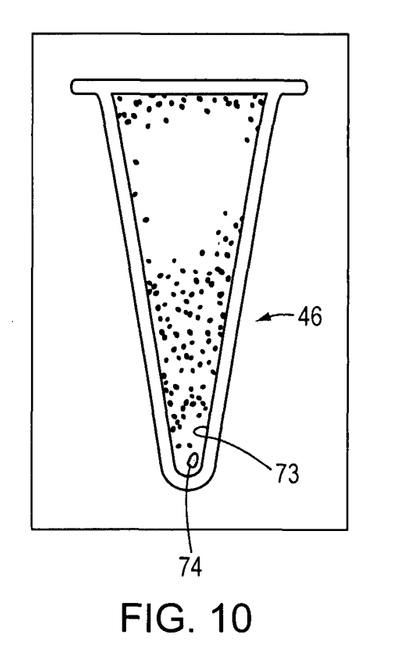

FIG. 9 depicts an exemplary pellet 74 formed with the use of the magnet array in FIG. 5. FIG. 10 depicts an exemplary pellet 74 formed with the use of the second magnet array 34 depicted in FIG. 6. The pellet 74 is formed in the same location with the use of either of the exemplary magnetic arrays 34 (not shown). The pellet 74 is formed by concentrating the magnetic field lines from the magnetic array 34 at the location of the vial wall 73 where the pellet 74 forms. Because of the high concentration of magnetic field lines, the specific complexes 43 (containing the magnetic particles, target molecules and markers) will be attracted to that region of the wall 73 and will clump together, eventually forming the pellet 74. The pellet 74, once extracted from the vial 46 and analyzed in the luminometer 32, may facilitate the analysis of the target molecules in the luminometer 32 (not shown).

In another embodiment (not shown), the magnetic washing module 30 comprises a vial chamber, which may be humidity regulated. The vial chamber is, for example, a rectangular box 75 that encloses the magnetic washing module 30. The vial chamber may be sealed once the vials 46 are placed in the vial receiving members 42. The sealed vial chamber does not permit the transfer of air in and out of the chamber. Alternatively, the clinical instrument analyzer system 20 is maintained within a housing and the humidity of the interior of the housing is regulated.

In one embodiment, the vial chamber prevents, for example, the vial 46 from contacting the ambient air and enables the moderation of the humidity in the vials 46 to provide a predetermined relative humidity. Humidity regulation or moderation may prevent unwanted particle aggregation prior to the desired aggregation into a pellet 74 of the specific complexes caused by the action of the magnetic field in the magnetic washing station 35. Sealing the vials 46 from outside air permits, for example, the monitoring of the humidity of the air immediately surrounding the vials 46. The level of humidity affects the performance of the magnetic washing module 30. In certain embodiments, a humidity detector determines the humidity inside the vial chamber. Once the humidity has been determined by the humidity detector, the humidity of the vial chamber may be altered and regulated, for example, by controlling the rate of fluid injection by the injector pipette 54 or the rate of aspiration by the aspirator pipette 44 into the vial 46.

In some embodiments, the aspirator 44 and injector pipettes 54 are used to ensure that the particles do not dry out or clump together prior to the application of the magnetic field. In one embodiment, after aspiration the injector pipette 44 dispenses a small amount of liquid into the vial 46 in the range of 15 to 20 µl.

In another embodiment, the aspirator pipette 44 is used to regulate the humidity. For example, the aspirator pipette 44 is submerged in the liquid contained within the vial 46. The depth of the aspirator pipette 44 ranges from, for example, just below the surface of the liquid contained within the vial to about 0.5 mm from the vial bottom. Once the aspirator pipette 44 is submerged, the aspirator pipette 44 removes liquid from the vial 46. The flow of liquid through the aspirator pipette 44 is in the range of, for example, 400 ml of liquid in 0.5 seconds to 400 μl in 5 seconds, alternatively 5 mL/min to 20 mL/min, preferably 10 mL/min. This low, gentle rate of flow may be accomplished through the use of, for example, a vacuum or peristaltic pump.

In some embodiments, the aspirator pipette 44 or the injector pipette 54 contain wash solution. The wash solution also may contain, for example, surfactants to reduce the surface tension in the solution thereby mitigating particle clumping.

The humidity control is not limited to these examples, but may be controlled by any known means of regulating humidity, such as injecting humid and/or dry air into the chamber, spraying a mist of water into the chamber and various other methods. The fluid may be injected into the chamber at a rate of 25 mL/min or 60 mL/min, depending on the diameter of the injector, or preferably in the range of 20 mL/min to 100 mL/min.

In another embodiment, the magnetic washing module 30 comprises a temperature regulator 77. The temperature regulator may insure that the temperature of the vial chamber remains at a predetermined, constant, and desired level.

In another aspect, the invention is directed to a method of washing magnetic particles used in a diagnostic assay conducted by a clinical instrument analyzer system 20. According to the method of the invention, an automated clinical instrument analyzer system 20 including a vial loader 22, a sample station (not shown), a reagent station (not shown), a carousel 28, a magnetic washing module 30, a plurality of pipettes 24, a luminometer 32 and a heater is provided. For example, the vial loader 22 loads a vial 46 onto the carousel 28. The vial 46 is carried from the vial loader 22 via the carousel 28 to a sample station. In an embodiment, the humidity is regulated.

At the sample station, a patient's sample, including the target molecules to be analyzed, is introduced to the vial 46. At the reagent station, antibodies against the target molecule, a marker substance containing, for example, luminogens and magnetizable particles are introduced to the vial 46. The marker substance and the magnetic particles are coated with specific antibodies to the target substance. The antibodies recognize and bind to the target molecule in the patient's sample in an immunochemical reaction. As a result, specific complexes 43 of magnetic particles, markers, and target molecules are formed. The vial 46 is incubated for a predetermined period of time and temperature according to the requirements of the assay.

Following incubation of the vial 46, the carousel 28 then transports the vial 46 to the magnetic washing module 30. The vial 46 is positioned in a vial holder 42, the vial holder 42 may be lowered or raised, and the magnetic field is applied. The magnetic field of the magnet array 34 in the magnet station 35 attracts the specific complexes 43 to the interior wall 73 of the vial 46 proximate to the magnet array 34. Then, the vial 46 is injected and aspirated one or more times with wash fluid through the aspirator pipette 44 and injector pipette 54. The vial 46 is rinsed one or more times by injection or aspiration to remove all remaining particles except for the particles complexed in the specific complexes 43.

Once the vial 46 has been washed several times, the magnetic field is removed by moving the magnet station 35, or the vial 46, or by moving the magnet station 35 and vial 46. Then, the carousel 22 transports the vial 46 to a luminometer 32. The luminometer 32 analyzes the vial sample for the specific complexes 43. Since the luminogen is attached to the target molecule in the patient sample in the specific complex 43, the user can readily ascertain the amount of target molecules in the sample, based on the luminescence of the pellet 74.

Variations, modification, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A system, for manipulating magnetic particles comprising:
   a vial;
   a receiving member comprising a magnetic array said magnetic array comprising a stack of at least three magnets and at least a spacer, and a spring finger; and,
   wherein the receiving member is configured for holding the vial containing magnetic particles,
   the vial being positioned in said receiving member between and directly contacted by the magnetic array and by the spring finger.

2. The system of claim 1 wherein said spacer is manufactured from materials selected from the group consisting of aluminum, plastic, carbon fiber, polymers, other non-magnetic materials, and combinations thereof.

3. The system of claim 1 wherein said magnet array is fixed to the receiving member.

4. The system of claim 1 wherein said magnet array is releasably attached to the receiving member.

5. The system of claim 1 wherein said magnets comprise neodymium-iron-boron.

6. The system of claim 1 further comprising a humidity regulator.

7. The system of claim 1 further comprising a temperature regulator.

8. The system of claim 1 further comprising one or more pipettes.

9. The system of claim 1 wherein each of said at least three magnets has a horizontal axis that is longer than a vertical axis.

10. The system of claim 6 wherein said vial comprises a chamber wherein said chamber is humidity regulated by said humidity regulator.

11. The system of claim 1 wherein said magnets comprise samarium-cobalt.

12. The system of claim 1 wherein said magnets comprise alnico.

13. The system of claim 1 wherein said magnets comprise and ferrite.

* * * * *

UNITED STATES PATENT AND TRADEMARK OFFICE
CERTIFICATE OF CORRECTION

PATENT NO. : 8,795,609 B2  Page 1 of 1
APPLICATION NO. : 11/704138
DATED : August 5, 2014
INVENTOR(S) : Garcia Gros et al.

It is certified that error appears in the above-identified patent and that said Letters Patent is hereby corrected as shown below:

In the Claims

Column 10, Line 56, claim 13, delete "and ferrite" and insert -- hard ferrite --

Signed and Sealed this
Twenty-first Day of October, 2014

Michelle K. Lee
*Deputy Director of the United States Patent and Trademark Office*